(12) United States Patent
Webb

(10) Patent No.: US 6,699,903 B2
(45) Date of Patent: Mar. 2, 2004

(54) MONOHYDRATE OF CIS-LITHIUM-CYANO-4-[3-(CYCLOPENTYLOXY)-4-METHOXYPHENYL] CYCLOHEXANECARBOXYLATE

(75) Inventor: Kevin Scott Webb, Port St. Lucie, FL (US)

(73) Assignee: SmithKline Beecham Corporation, Philadelphia, PA (US)

( * ) Notice: Subject to any disclaimer, the term of this patent is extended or adjusted under 35 U.S.C. 154(b) by 18 days.

(21) Appl. No.: 10/181,865
(22) PCT Filed: Jan. 18, 2001
(86) PCT No.: PCT/US01/01487
§ 371 (c)(1), (2), (4) Date: Jul. 22, 2002
(87) PCT Pub. No.: WO01/55094
PCT Pub. Date: Aug. 2, 2001

(65) Prior Publication Data
US 2003/0032670 A1 Feb. 13, 2003

Related U.S. Application Data
(60) Provisional application No. 60/178,129, filed on Jan. 26, 2000.

(51) Int. Cl.[7] .................. C07C 255/50
(52) U.S. Cl. ............. 514/521; 558/426
(58) Field of Search .................. 558/426

(56) References Cited

U.S. PATENT DOCUMENTS

| 5,552,438 A | 9/1996 | Christensen, IV |
| 5,602,157 A | 2/1997 | Christensen, IV |

*Primary Examiner*—Joseph K. McKane
*Assistant Examiner*—Kamal Saeed
(74) *Attorney, Agent, or Firm*—James M. Kanagy; Stephen Venetianer; Charles M. Kinzig

(57) ABSTRACT

This invention provides a means for preparing a monohydrate of the lithium salt of cis 4-cyano-4-[3-(cyclopentyloxy)-4-methoxyphenyl] cyclohexanecarboxylate which is a novel composition of matter.

3 Claims, 4 Drawing Sheets

Mass Spectral Fragmentation Pathway for lot KW-27173-68C0

[m/z 210] (1.1%)

[m/z 171] (0.6%)

MONOHYDRATE OF CIS-LITHIUM-CYANO-4-[3-(CYCLOPENTYLOXY)-4-METHOXYPHENYL]CYCLOHEXANECARBOXYLATE

This application claims the benefit of provisional application No. 60/178,129 filed Jan. 26, 2000.

AREA OF THE INVENTION

This invention relates to the preparation of a monohydrate of the lithium salt of cis 4-cyano-4-[3-(cyclopentyloxy)-4-methoxyphenyl]cyclohexanecarboxylate, and the hydrate per se.

BACKGOUND OF THE INVENTION

Cyclic nucleotide phosphodiesterases (PDEs) represent a family of enzymes that hydrolyze the ubiquitous intracellular second messengers, adenosine 3',5'-monophosphate (cAMP) and guanosine 3',5'-monophosphate (cGMP) to their corresponding inactive 5'-monophosphate metabolites. At least ten distinct classes of PDE isozymes are believed to exist, each possessing unique physical and kinetic characteristics and each representing a product of a different gene family. These are distinguished using Arabic numerals 1–10.

A new approach toward improving the side effect profile of PDE inhibitors is to design a new generation of compounds that inhibit only a single PDE isozyme, i.e., the PDE isozyme that predominates in the tissue of cell of interest. The predominate cAMP PDE isozyme in immune and inflammatory cells is PDE4. It is also a major regulator of cAMP content in airway smooth muscle. Thus, selective inhibition of PdE4 elevates cAMP content in immune and inflammatory cells, as well as in airway smooth muscle. This leads to anti-inflammatory effects as well as bronchodilation. One or both of these therapeutic actions are useful in treating a variety of diseases, including, but not limited to asthma and COPD. PDE4 inhibitors, particularly PDE4-specific inhibitors are useful also in treating other diseases in the area of inflammation, (e.g., asthma, chronic obstructive pulmonary disease, inflammatory bowel disease, rheumatoid arthritis), affects related to tumor necrosis factor and to cognition impairment (e.g., multi-infarct dementia, cognitive dysfunction, or stroke). This invention relates to a compound that is better tolerated than previous PDE4 inhibitors, namely cis-4-cyano-4-[3-(cyclopentyloxy)-4-metboxyphenyl]cyclohexane-1-carboxylic acid. More specifically this invention provides the hydrate of the lithium salt of this acid.

SUMMARY OF THE INVENTION

This invention relates to cis-lithium 4-cyano-4-[3-(cyclopentyloxy)-4-methoxyphenyl]cyclohexanecarboxylate monohydrate which has the structure represented by Formula (I):

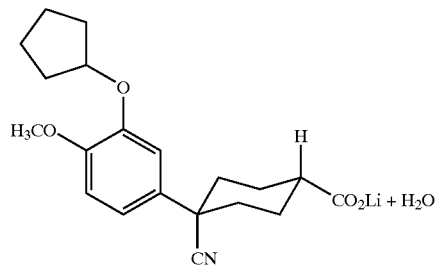

and a process for preparing it, as described below.

Specific Exemplification

A process for preparing cis-4-cyano-4-[3-(cyclopentyloxy)-4-methoxyphenyl]cyclohexane-1-carboxylic acid is described in several publications. See for example U.S. Pat. No. 5,552,438 issued Sep. 3, 1996 and pending PCT application number PCT/US98/02749 published on Aug. 13, 1998 as WO 98/34584 or PCT application US98/21-61 published Apr. 22, 1999 as WO 99/18793. These publications, and others, teach how to make the Li salt of said acid. But those processes do not result in the preparation of a hydrate of the Li salt, including a monohydrate.

EXAMPLE 1

A lot of anhydrous lithium salt of the acid was prepared by the process detailed in the afore-mentioned PCT applications WO 98/34584 and WO 99/18793. The lot was crystallized from 80 mL of acetonitrile and 4 mL of water and rinsed with 9.5 mL of acetonitrile and 0.5 mL of water. The filter cake was then crystallized from acetonitrile and 4 mL of water and rinsed with 9.50 mL of acetonitrile and 0.5 mL of water. The material was dried in a vacuum oven (50° C., 20 inches) for 48 hours to provide the monohydrate.

Appearance: white powder.

Ultraviolet Spectroscopy

Figure 1:
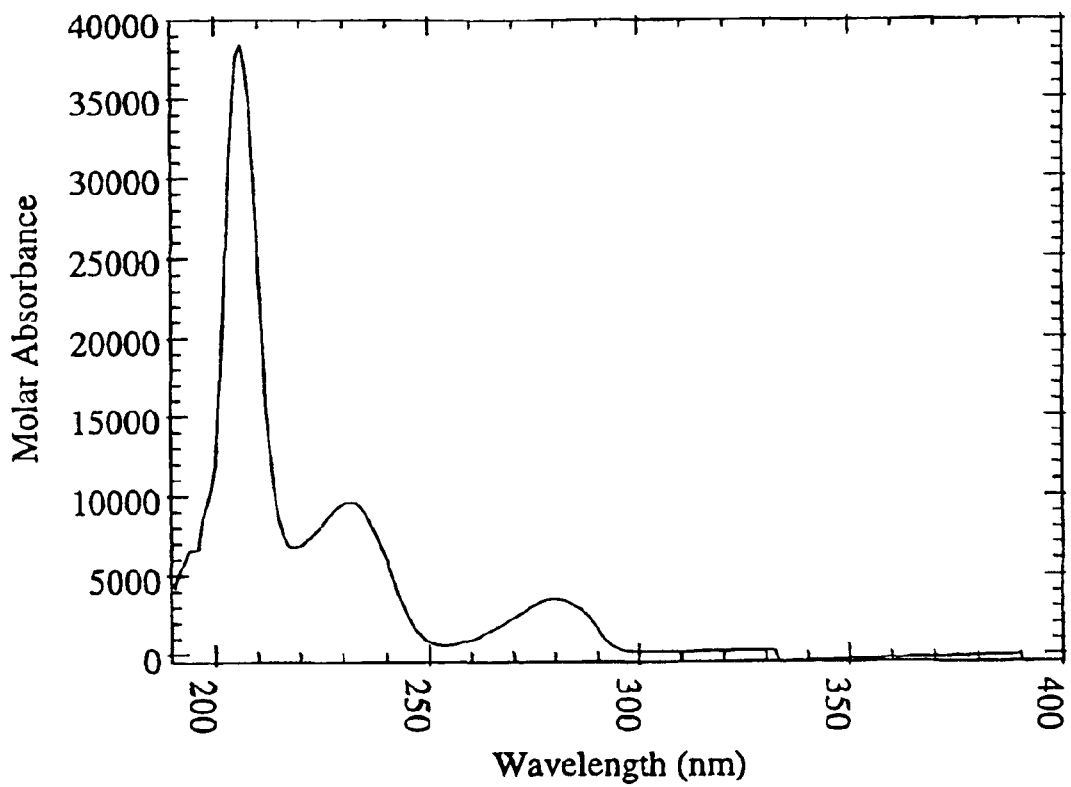
FIG. 1 is an ultraviolet spectrum for the Li monohydrate salt

The ultraviolet absorption spectrum of the monohydrate was measured using a Perkin-Elmer Lambda 7 spectrophotometer, for a solution of 0.0076 mg/mL in methanol. The spectrum is dominated by the aromatic chromophore and conforms to other compounds in the series as shown in Table 1 and FIG. 1.

TABLE 1

| Ultraviolet Absorption Bands | | |
|---|---|---|
| Wavelength (nm) | ε | Assignment |
| 206 | 38,400 | $^1B$ (aromatic) |
| 231 | 9,600 | $^1L_a$ |
| 280 | 3,500 | $^1L_b$ |

Infrared Spectroscopy

Figure 2:
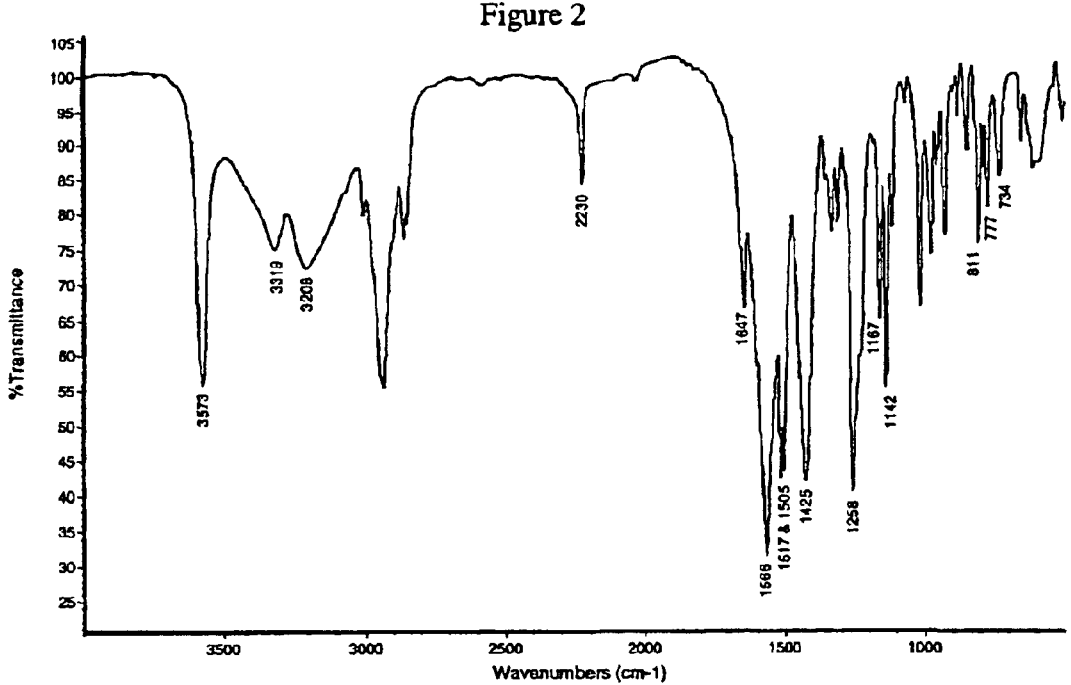
FIG. 2 is an infrared spectrum of the Li monohydrate salt.

The infrared absorption spectrum of the monohydrate Li salt was obtained as a potassium bromide pellet using a Nicolet Magna 760 FT-IR spectrometer. The spectrum was measured with a resolution of 4 $cm^{-1}$. The spectrum had band assignments shown in Table 2. The infrared spectrum is shown in FIG. 2.

TABLE 2

Infrared Band Assignments for lot KW-27173-68C0

| Wavenumber (cm$^{-1}$) | Assignment |
| --- | --- |
| 3573 | O—H stretch (water) |
| 3319, 3208 | O—H stretch (water of hydration) |
| 3100–3000 | =C—H stretches |
| 3000–2800 | —C—H stretches |
| 2230 | nitrile stretch |
| 1647 | C=O stretch (acid) |
| 1566 | C=O stretch (carboxylate) and C=C stretches |
| 1517, 1505 | C=C stretches |
| 1425 | C—H deformation and C=C stretches |
| 1258, 1167, 1142 | C—O stretches |
| 811, 777, 734 | aromatic C—H deformations |

EXAMPLE 2

Karl Fischer Titration

Water was determined by Karl Fischer titration. A Mettler DL18 instrument was used to carry out the determination. Reagents were obtained from Cresent Chemical Co., Hauppauge, N.Y., USA and carried the tradename Hydranal (standard: sodium tartraqte-2-hydrate; titrant; and solvent). Water content was found to be 5.14% w/w, which agreed with the theoretical value for one molecule of water (4.91% w/w).

EXAMPLE 3

Thermogravimetric Analysis

The TG analysis of the lot prepared in Example 1 was conducted using standard procedures. A total weight loss of 4.96% was observed at approximately 137° C. This weight loss is consistent with that of a monohydrate.

EXAMPLE 4

NMR Spectroscopy

Figure 3:
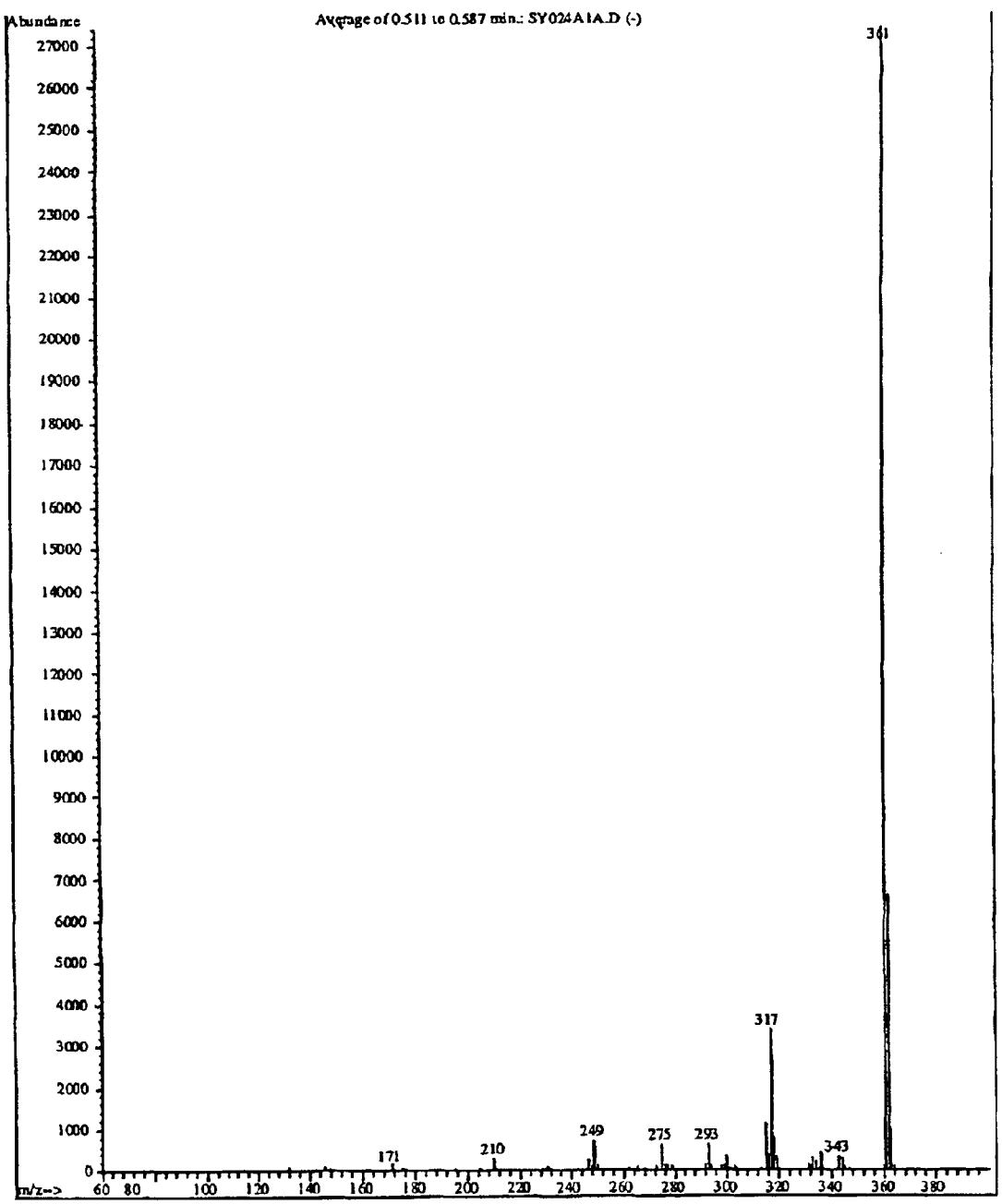
FIG. 3 is a tracing of a MS output for Formula (I) monohydrate
Figure 4:
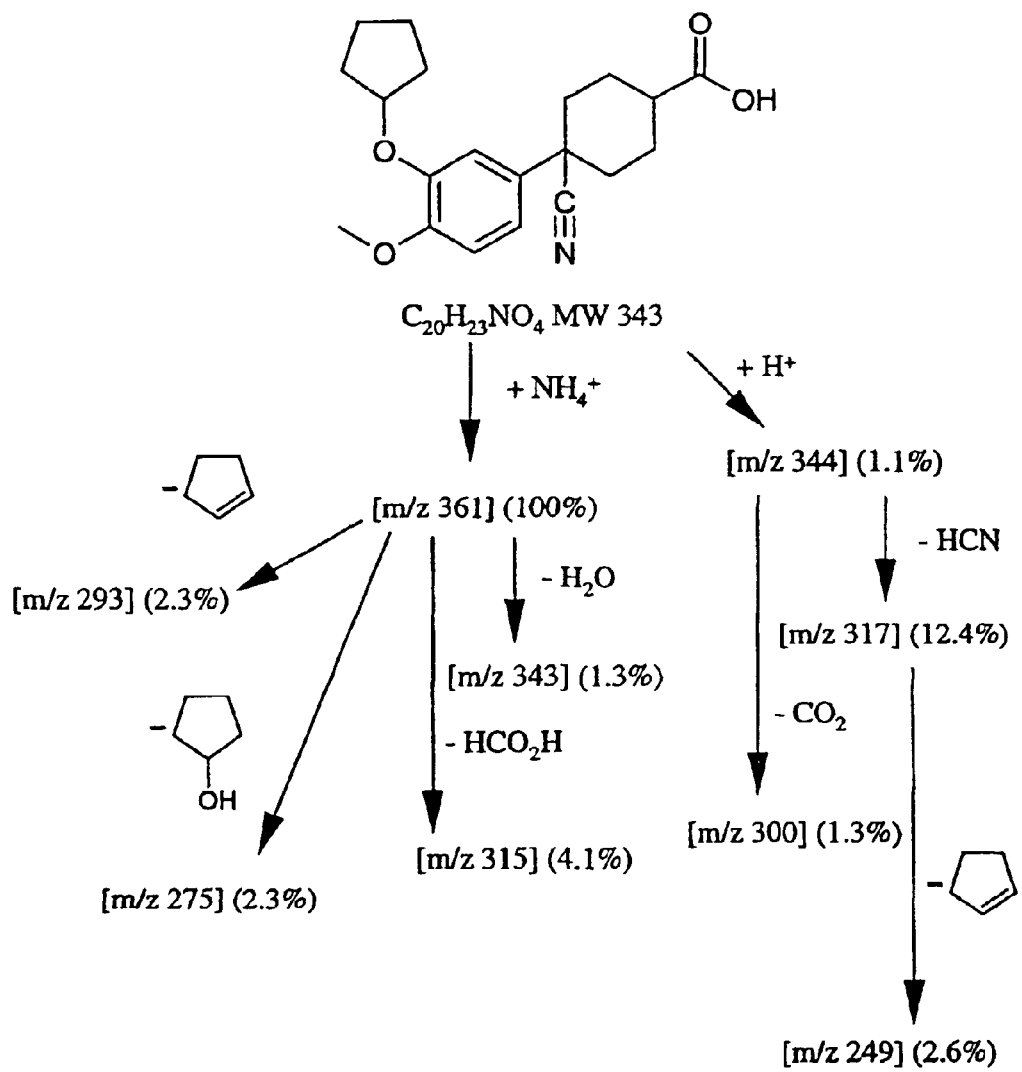
FIG. 4. is a flowchart of the MS ionization products for Formula (I) monohydrate.
Figure 4:
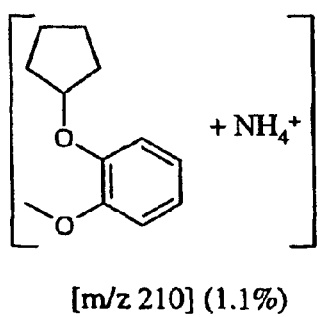
Figure 4:
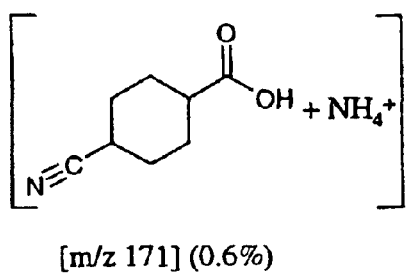

The $^1$H and $^{13}$C NMR spectra of the lithium salt monohydrate were measured at 400.13 MHz and 100.63 MHz, respectively, using a Bruker Instruments AMX 400 spectrometer maintained at 25° C. The sample was prepared by dissolving 20.1 mg in 0.8 mL of DMSO-d$_6$ (99.96 atom % D, ISOTEC), and the spectra were referenced to tetramethylsilane as a secondary solvent reference. The proton and $^{13}$C GASPE ($^{13}$C multiplicity editing via a GAted Spin Echo sequence) NMR spectra are shown in FIGS. 3 and 4, and the $^1$H and $^{13}$C data are consistent with the structure of a lithium salt monohydrate of Formula (I).

Homonuclear two-dimensional information used for structural assignments include COSY (COrrelation SpectroscopY) data which were used to identify the members of each proton spin system and NOESY (Nuclear Overhauser Effect SpectroscopY) data which indicated through-space nOe interactions. The nOe data helped to establish the spatial relationship between the individual spin systems and to define the stereochemical relationship between the 1- and 4-substituents. Heteronuclear two-dimensional information used for structural assignments include HMQC (Heteronuclear Multiple Quantum Coherence) data that allowed for assignment of the protonated $^{13}$C signals via one bond correlations and HMBC (Heteronuclear Multiple Bond Coherence) data that allowed for assignment of quaternary $^{13}$C signals via multiple bond correlations. The HMBC data also served to verify all of the previous $^1$H and $^{13}$C assignments. The chemical shift assignments for the monohydrate salt in DMSO-d$_6$ is summarized in Table 3.

TABLE 3

| $^{13}$C Position | $^{13}$C Chemical Shift, δ (multiplicity) | $^1$H Chemical Shift, δ (integration) | $^1$H Multiplicity (J = Hz) |
| --- | --- | --- | --- |
| 5 | 178.9 (s) | | |
| 4' | 149.2 (s) | | |
| 3' | 147.0 (s) | | |
| 1' | 133.7 (s) | | |
| CN | 123.1 (s) | | |
| 6' | 117.5 (d) | 6.99 (1H) | dd (J = 2.3, 9.2 Hz) |
| 2' | 112.7 (d) | 7.00 (1H) | d (J = 2.3 Hz) |
| 5' | 112.2 (d) | 6.93 (1H) | d (J = 9.2 Hz) |
| 1" | 79.6 (d) | 4.81 (1H) | m |
| CH$_3$O | 55.6 (q) | 3.72 (3H) | s |
| 1 | 44.5 (d) | 1.96 (1H) | m |
| 4 | 43.0 (s) | | |
| 3 | 36.5 (2C, t) | 2.06 (2H) | m |
| | | 1.76 (2H) | m |
| 2" | 32.2 (2C, t) | 1.87 (2H) | m |
| | | 1.69 (2H) | m |
| 2 | 27.5 (2C, t) | 2.01 (2H) | m |
| | | 1.63 (2H) | m |
| 3" | 23.6 (2C, t) | 1.69 (2H) | m |
| | | 1.56 (2H) | m |

EXAMPLE 5

Desorption Chemical Ionization Mass Spectrometry

The desorption chemical ionization mass spectrum (DCI/MS) of the lithium salt monohydrate was obtained using a Nermag R30-10 triple quadrupole mass spectrometer. A 1:1 methanol:methylene chloride solution of the monohydrate was prepared at a concentration of 0.1 mg/mL. The sample was introduced into the mass spectrometer using a DCI probe. The probe was heated at a rate of 20° C./s. The reagent gas was ammonia. The mass spectrum was scanned from 60 to 860 Da at a rate of 1.0 scans/s. The mass spectrum was acquired using a Mass Evolution EZScan data system and processed using the HP MS ChemStation software (FIG. 3).

The following molecular ion adducts were observed: [M+H]$^+$ at m/z 344 and [M+NH$_4$]$^+$ at m/z 361. Plausible ionic structures for the observed fragments that are consistent with the structure of Formula (I) monohydrate are given in FIG. 4.

What is claimed is:

1. A compound which is the monohydrate of the lithium salt of cis 4-cyano-4-[3-(cyclopentyloxy)-4-methoxyphenyl]cyclohexanecarboxylate.

2. A pharmaceutical preparation consisting of the monohydrate of the lithium salt of cis 4-cyano-4-[3-(cyclopentyloxy)-4-methoxyphenyl]cyclohexanecarboxylate and a pharmaceutically acceptable expicient.

3. A method for preparing the monohydrate of the lithium salt of cis 4-cyano-4-[3-(cyclopentyloxy)-4-methoxyphenyl]cyclohexanecarboxylate, which method comprises treating an aliquot of anydrous lithium salt with acetonitrile and water.

* * * * *